(12) United States Patent
Heyse et al.

(10) Patent No.: US 6,274,113 B1
(45) Date of Patent: *Aug. 14, 2001

(54) INCREASING PRODUCTION IN HYDROCARBON CONVERSION PROCESSES

(75) Inventors: John V. Heyse, Crockett; Daniel P. Hagewiesche, Oakland, both of CA (US); Paul M. Spindler, Kingwood, TX (US)

(73) Assignee: Chevron Phillips Chemical Company LP, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/362,593

(22) Filed: Jul. 28, 1999

Related U.S. Application Data

(62) Division of application No. 08/848,767, filed on May 1, 1997, now abandoned, which is a continuation of application No. 08/496,488, filed on Jun. 29, 1995, now Pat. No. 5,658,452, which is a continuation-in-part of application No. 08/365,855, filed on Dec. 28, 1994, now Pat. No. 5,648,178, which is a continuation-in-part of application No. 08/269,764, filed on Jul. 1, 1994, now Pat. No. 5,575,902, which is a continuation-in-part of application No. 08/177,822, filed on Jan. 4, 1994.

(51) Int. Cl.$^7$ .............................. C01B 3/24; C10G 75/00
(52) U.S. Cl. ...................... 423/418.2; 423/650; 252/373; 208/48 R
(58) Field of Search .................. 423/418.2, 650; 252/373; 208/48 R

(56) References Cited

U.S. PATENT DOCUMENTS

| | | |
|---|---|---|
| 1,802,695 | 4/1931 | Bennett . |
| 1,883,630 | 10/1932 | Duff . |
| 2,063,596 | 12/1936 | Feilen . |
| 2,263,366 | 11/1941 | Peck et al. . |
| 2,685,543 | 8/1954 | Sineband . |
| 2,818,374 | 12/1957 | Certa et al. . |
| 2,929,775 | 3/1960 | Aristoff et al. . |
| 3,108,013 | 10/1963 | Chao et al. . |
| 3,160,671 | 12/1964 | Feigelman . |
| 3,169,000 | 2/1965 | Earnst et al. . |
| 3,178,321 | 4/1965 | Satterfield . |
| 3,284,526 | 11/1966 | Frayer . |
| 3,459,821 | 8/1969 | Engelbrecht . |
| 3,505,028 | 4/1970 | Douthit . |
| 3,531,394 | 9/1970 | Kuszman . |
| 3,531,543 | 9/1970 | Clippinger et al. . |
| 3,536,776 | 10/1970 | Lo . |
| 3,584,060 | 6/1971 | Rausch . |
| 3,607,960 | 9/1971 | Button . |
| 3,617,359 | 11/1971 | Wakefield . |
| 3,623,901 | 11/1971 | Forstmann et al. . |
| 3,631,215 | 12/1971 | Clippinger et al. . |
| 3,634,147 | 1/1972 | Helwig . |
| 3,686,340 | 8/1972 | Patrick et al. . |
| 3,700,745 | 10/1972 | Kovach et al. . |
| 3,743,551 | 7/1973 | Sanderson . |
| 3,767,456 | 10/1973 | Glaski . |
| 3,835,183 | 9/1974 | Carpenter et al. . |
| 3,864,284 | 2/1975 | Clippinger et al. . |
| 3,878,131 | 4/1975 | Hayes . |
| 3,890,110 | 6/1975 | Glaski . |
| 3,890,686 | 6/1975 | Caubet . |
| 3,919,073 | 11/1975 | Bagnoli et al. . |
| 3,944,396 | 3/1976 | Chivinsky . |
| 3,955,935 | 5/1976 | Shockbey . |
| 3,966,833 | 6/1976 | Cosyns et al. . |
| 4,013,487 | 3/1977 | Ramqrist et al. . |
| 4,015,950 | 4/1977 | Galland et al. . |
| 4,019,969 | 4/1977 | Golebiowski et al. . |
| 4,058,452 | 11/1977 | Loboda . |
| 4,111,763 | 9/1978 | Pryor . |
| 4,132,743 | 1/1979 | Caster et al. . |
| 4,161,510 | 7/1979 | Edridge . |
| 4,163,706 | 8/1979 | Horowitz et al. . |
| 4,167,532 | 9/1979 | Walker et al. . |
| 4,167,533 | 9/1979 | Raymond . |
| 4,173,457 | 11/1979 | Smith . |
| 4,179,361 | 12/1979 | Michlmayr . |
| 4,189,613 | 2/1980 | Bjornson . |
| 4,191,632 | 3/1980 | Cosyns et al. . |

(List continued on next page.)

FOREIGN PATENT DOCUMENTS

| | | |
|---|---|---|
| 0 082 920 | 7/1983 | (EP) . |
| 0 146 081 | 6/1985 | (EP) . |
| 0 192 059 | 8/1986 | (EP) . |
| 0 351 067 | 1/1990 | (EP) . |
| 0 403 976 | 12/1990 | (EP) . |
| 0 313 303 | 8/1929 | (GB) . |
| 0 317 303 | 8/1929 | (GB) . |
| 1 054 121 | 1/1967 | (GB) . |
| 1 122 017 | 7/1968 | (GB) . |
| 1 149 163 | 4/1969 | (GB) . |
| 2 066 696 | 7/1981 | (GB) . |
| 1 604 604 | 12/1981 | (GB) . |
| 2 162 082 | 1/1986 | (GB) . |
| 2 234 530 | 2/1991 | (GB) . |
| WO92/15653 | 9/1992 | (WO) . |
| WO94/15896 | 7/1994 | (WO) . |

OTHER PUBLICATIONS

Alon Processing, Inc.; "Alonized Steels for high temperature corrosion resistance"; 1990; pp. 1–19.

(List continued on next page.)

Primary Examiner—Bekir L. Yildirim
(74) Attorney, Agent, or Firm—Pennie & Edmonds LLP

(57) ABSTRACT

A improved hydrocarbon conversion process, comprising applying a plating, cladding, paint or other coating to at least a portion of a hydrocarbon conversion reactor system which is used to convert hydrocarbons to products in the presence of steam, said coating being effective to reduce the amount of undesirable by-products in said process; and operating the hydrocarbon conversion process at a steam to hydrocarbon ratio that is lower than the steam to hydrocarbon ratio at which said process was operated prior to applying said coating. Preferred hydrocarbon conversion process includes steam cracking of hydrocarbons to produce ethylene and dehydrogenation of ethylbenzene to styrene.

18 Claims, No Drawings

U.S. PATENT DOCUMENTS

| | | |
|---|---|---|
| 4,191,846 | 3/1980 | Farha, Jr. et al. . |
| 4,204,997 | 5/1980 | Hobbs et al. . |
| 4,208,302 | 6/1980 | McKay . |
| 4,215,231 | 7/1980 | Raymond . |
| 4,220,560 | 9/1980 | Anquetil et al. . |
| 4,264,433 | 4/1981 | McKay . |
| 4,268,188 | 5/1981 | Bertus et al. . |
| 4,271,008 | 6/1981 | Vogt et al. . |
| 4,297,150 | 10/1981 | Foster et al. . |
| 4,350,719 | 9/1982 | Baldi . |
| 4,385,645 | 5/1983 | Campbell et al. . |
| 4,404,087 | 9/1983 | Reed et al. . |
| 4,410,418 | 10/1983 | Kukes et al. . |
| 4,438,288 | 3/1984 | Imai et al. . |
| 4,444,732 | 4/1984 | Konoki et al. . |
| 4,447,316 | 5/1984 | Buss . |
| 4,451,687 | 5/1984 | Daly et al. . |
| 4,456,527 | 6/1984 | Buss et al. . |
| 4,463,206 | 7/1984 | Derrien et al. . |
| 4,467,016 | 8/1984 | Baldi . |
| 4,471,151 | 9/1984 | Kolts . |
| 4,481,264 | 11/1984 | Faure . |
| 4,488,578 | 12/1984 | Tseung et al. . |
| 4,507,196 | 3/1985 | Reed et al. . |
| 4,511,405 | 4/1985 | Reed et al. . |
| 4,545,893 | 10/1985 | Porter et al. . |
| 4,551,227 | 11/1985 | Porter et al. . |
| 4,552,643 | 11/1985 | Porter et al. . |
| 4,555,326 | 11/1985 | Reid . |
| 4,595,673 | 6/1986 | Imai et al. . |
| 4,613,372 | 9/1986 | Porter et al. . |
| 4,665,267 | 5/1987 | Barri . |
| 4,666,583 | 5/1987 | Porter et al. . |
| 4,685,427 | 8/1987 | Tasson et al. . |
| 4,686,201 | 8/1987 | Porter et al. . |
| 4,687,567 | 8/1987 | Porter et al. . |
| 4,692,234 | 9/1987 | Porter et al. . |
| 4,692,313 | 9/1987 | Watanabe et al. . |
| 4,716,143 | 12/1987 | Imai . |
| 4,717,700 | 1/1988 | Venkstram et al. . |
| 4,727,216 | 2/1988 | Miller . |
| 4,741,819 | 5/1988 | Robinson et al. . |
| 4,743,318 | 5/1988 | Fischer et al. . |
| 4,762,681 | 8/1988 | Tansen et al. . |
| 4,786,625 | 11/1988 | Imai et al. . |
| 4,795,732 | 1/1989 | Barri . |
| 4,804,446 | 2/1989 | Lashmore et al. . |
| 4,804,487 | 2/1989 | Reed et al. . |
| 4,827,072 | 5/1989 | Imai et al. . |
| 4,830,732 | 5/1989 | Mohr et al. . |
| 4,863,892 | 9/1989 | Porter et al. . |
| 4,902,849 | 2/1990 | McKay et al. . |
| 4,917,969 | 4/1990 | Pircher et al. . |
| 4,925,549 | 5/1990 | Robinson et al. . |
| 4,926,005 | 5/1990 | Olbrich et al. . |
| 4,935,566 | 6/1990 | Dessau et al. . |
| 4,940,828 | 7/1990 | Petterson et al. . |
| 4,976,932 | 12/1990 | Maeda et al. . |
| 4,982,047 | 1/1991 | Barri et al. . |
| 5,012,027 | 4/1991 | Abrevaya et al. . |
| 5,015,358 | 5/1991 | Reed . |
| 5,053,572 | 10/1991 | Kim et al. . |
| 5,053,574 | 10/1991 | Tsutsui et al. . |
| 5,118,028 | 6/1992 | Ogawa et al. . |
| 5,139,814 | 8/1992 | Sugaro . |
| 5,139,914 | 8/1992 | Tomiyama et al. . |
| 5,196,632 | 3/1993 | Larsen et al. . |
| 5,238,492 | 8/1993 | Itoh et al. . |
| 5,242,665 | 9/1993 | Maeda et al. . |
| 5,298,091 | 3/1994 | Edwards, III et al. . |
| 5,405,525 | 4/1995 | Heyse et al. . |
| 5,406,014 | 4/1995 | Heyse et al. . |
| 5,413,700 | 5/1995 | Heyse et al. . |
| 5,575,902 | 11/1996 | Heyse et al. . |
| 5,648,178 | 7/1997 | Heyse et al. . |
| 5,658,452 | 8/1997 | Heyse et al. . |
| 5,849,969 | 12/1998 | Heyse et al. . |
| 5,866,743 | 2/1999 | Heyse et al. . |

OTHER PUBLICATIONS

Berg et al., "Catalytic LPG Dehydrogenation Fits in '80s Outlook"; Oil and Gas Journal; pp. 191–197; Nov. 1980.

Dunn, "HP In Construction"; Hydrocarbon Processing; pp. 41–42; Aug. 1991.

General Motors, "The Carbon Gradient.".

Gussow et al., "Dehydrogenation Links LPG to More Octanges"; Oil and Gas Journal; pp. 96–101; Dec. 1980.

W.A. McGill and M.J. and Weinbaum, "The Selection, Application and Fabrication of Alonized Systems in the Refinery Environment"; 1975; pp. 1–18.

Micron, Inc., Analytical Service Laboratory; "Report #R–8126, Alonzied Steel"; Jun. 1985.

Pujado et al., "Make $C_3$–$C_4$ Olefins Selectively"; Hydrocarbon Processing; pp. 65–70; Mar. 1990.

Pujado et al., "Production of LPG Olefins by Catalytic Dehydrogenation"; Energy Progress; vol. 4, No. 3; pp. 186–191; Sep. 1984.

Pujado et al., "OGJ Report"; Oil and Gas Journal; pp. 71–74; Mar. 1983.

Shinohara, Kohchi, Shibata, Sugitani and Tsuchida; "Development of nondestructive technique for measuring carburization thickness and a new carburization–resistant alloy"; Werkstoffe und Korrosion, 1986; pp. 410–411.

Toyo Engineering Corp. and Kubota; "CORET, New Cracking Tube to Retard Coke Depositions"; Mar. 1986; pp. 1–5.

Toyo Engineering Corp. and Kubota; "Development of Double–Layer Cast Tube for Anti–Caraburization and the Retarding of Code Deposition"; pp. 1–11.

King et al., "The Production of Ethylene by the Decomposition of n–Butane; the Prevention of Carbon Formation by the Use of Chromium Plating", Transactions of the E. I. C., vol. 3, No. 1, p. 1, (1959).

Platt's International Petrochemical Report (Oct. 1993).

J. R. Bernard, "Hydrocarbons Aromatization on Platinum Alkaline Zeolites", Proceedings of the Fifth Int. Conf. Zeolites, pp. 686–695, Heydon, London (1980).

J. Shinohara et al., "Development of Nondestructive Technique for Measuring Carburization Thickness and of a New Carburization Resistant Alloy," Workstoffe and Korrozion 37, (no month 1986), pp. 410–411.

"Report of the Panel on High Temperature Carburization to the Subcommitte on Corrosion", May 1963 (unclear whether a publication).

Robert Schueler, Hydrocarbon Processing, Aug. 1972.

R. Hochman and J. Burson III, Proceedings Division of Refining, "The Fundamentals of Metal Dusting", vol. 46 (1966).

G. L. Swales, "High Temperature Corrosion Problems in the Petroleum Refining and Petrochemical Industries", pp. 45–82 (no date).

R. F. Hochman, "Catastrophic Deterioration of High Temperature Alloys in Carbonaceous Atmospheres", pp. 715–732, Proceedings of the Symposium on Properties of High Temperature Alloys, 1978.

Hettinger, Keith, Gring and leter, Industrial and Engineering Chemistry, "Hydroforming Reactions, Effect of Certain Catalyst Properties and Poisons", Apr. 1955.

F.A. Prange, Corrosion, "Corrosion in a Hydrocarbon Conversion System", vol. 15, Dec. 1959.

C.J. Polk, "Evaluating Catalytic Reformer Heating Tubing After Extended High–Temperature Service", Nat'l Assoc. of Corros. Engineers, Paper No. 50, Mar. 1980.

excerpts from NPRA (National Petroleum Refiners Assoc. Q&A, 1981 (Questions 17 & 21).

pp. 62–65 from 1980 PEP Report, "Reforming for BTX". SRI International.

R. G. McClung, Oil & Gas Journal, pp. 98 & 99 (Oct. 1990).

D.M. Little, Catalytic Reforming, pp. 136–141. No Date.

excerpts from NRPA, Q&A, 1982 (Question 21).

Buss et al., "New Developments in Rheniforming", 1978 NPRA Annual Meeting (1978).

Freiburger et al., "Recent Catalyst and Process Improvements in Commercial Rheniforming", 1980 NRPA Annual Meeting (1980).

INCREASING PRODUCTION IN HYDROCARBON CONVERSION PROCESSES

This application is a divisional application of Ser. No. 08/848,767, filed May 1, 1997, now abandoned which is a continuation of Ser. No. 08/496,488 filed Jun. 29, 1995 (now U.S. Pat. No. 5,658,452), which is a continuation-in-part of Ser. No. 08/365,855, filed Dec. 28, 1994 (now U.S. Pat. No. 5,648,178), which is a continuation-in-part of Ser. No. 08/269,764, filed Jul. 1, 1994 (now U.S. Pat. No. 5,575,902), which is a continuation-in-part of Ser. No. 08/177,822 filed Jan. 4, 1994. The contents of all of these applications are hereby incorporated by references in their entirety.

FIELD OF INVENTION

The invention pertains to novel ways to operate hydrocarbon conversion processes at reduced steam to hydrocarbon ratios utilizing a metal passivation layer on the surface of a steel substrate. In one aspect, the invention relates to the production of ethylene by cracking hydrocarbons in the presence of steam, preferably at reduced steam levels, while preventing catalytic coking. In another aspect, the invention relates to the formation of styrene by dehydrogenation of ethylbenzene under reduced steam conditions.

BACKGROUND OF THE INVENTION

Coking and carburization are problems in a variety of high temperature hydrocarbon conversion processes. Recently, new coatings have been disclosed that prevent carburization in some of these processes. For example, U.S. Pat. No. 5,405,525 to Heyse et al. discloses a method for reforming hydrocarbons comprising coating portions of a reactor system with a material more resistant to carburization, reacting the material with metal sulfides existing in the portions of the reactor system prior to coating, fixating and removing at least a portion of the sulfur in the metal sulfides, and reforming hydrocarbons in the reactor system under conditions of low sulfur.

Similarly, U.S. Pat. No. 5,413,700 to Heyse et al. discloses a method for reforming hydrocarbons comprising coating portions of a reactor system with a material more resistant to carburization, reacting the material with metal oxides existing in the portions of the reactor system prior to coating, fixating or removing at least a portion of the oxide in the metal oxides, and reforming hydrocarbons in the reactor system under conditions of low sulfur.

Also, U.S. Pat. No. 5,406,014 to Heyse et al. discloses methods for dehydrogenation of alkanes into alkenes in reactor systems of improved resistance to carburization under dehydrogenation conditions. The reactor walls are provided with a carburization and abrasion resistant protective layer by applying a metal plating, cladding or other coatings, such as painting, of a metal, such as Sb, As, Bi, Cu, Cr, Ga, Ge, In, Pb, Se, Te, Sn, particularly tin as a stannide layer, for forming a carburization resistant protective layer to a thickness of about 0.5 to 15 mils, effective to isolate the steel portion from hydrocarbons during the dehydrogenation process while avoiding any substantial liquid metal embrittlement. The protective layer is formed anchored to the steel portion through an intermediate carbide-rich bonding layer. The invention can be applied to conversion of ethylbenzene to styrene. This patent does not discuss changing the steam to hydrocarbon ratio.

Problems associated with carburization include coking, carburization of system metallurgy, and metal dusting. The embrittlement of the steel walls by carburization leads to "metal-dusting", i.e., a release of catalytically active particles and liquid droplets of metal due to an erosion of the metal. The excessive "metal-dusting" adds active metal particulates to the system, which particulates provide additional sites for coke formation.

One solution to the problems associated with carburization, embrittlement, and metal-dusting is to add steam and often sulfur as well to the feed to thereby effectively inhibit carburization. However, the addition of either steam or sulfur increases production cost and process complexity.

Nonetheless, some high temperature hydrocarbon conversion processes utilize steam, often in large amounts. These processes include thermal cracking of light and heavy hydrocarbons to ethylene and propylene; the conversion of ethylbenzene to styrene; and the steam reforming of hydrocarbons such as natural gas to hydrogen and other products, and the dehydrogenation of butene to produce butadiene.

In the production of ethylene by thermal cracking, a diluent fluid such as steam is usually combined with a hydrocarbon feed such as ethane and/or propane and/or naphtha, and introduced into a cracking furnace. Within the furnace, the feed stream which has been combined with the diluent fluid is converted to a gaseous mixture which primarily contains hydrogen, methane, ethylene, propylene, butadiene, and small amounts of heavier gases. At the furnace exit this mixture is cooled to remove most of the heavier gases, and then compressed. The compressed mixture is routed through various distillation columns where the individual components such as ethylene are separated and purified.

Steam serves a variety of purposes. It is a diluent used in order to improve yields. It drives the hydrocarbon through the system. In the case of ethylene plants, it oxidizes the steel somewhat, and inhibits metal-catalyzed coking on the furnace tube walls.

One recognized problem in the production of ethylene by thermal cracking is coke formation. Because coke is a poor thermal conductor, as coke is deposited, higher furnace temperatures are required to maintain the gas temperature in the cracking zone at necessary levels. Higher temperatures increase feed consumption and shorten tube life. Also, cracking operations are typically shut down periodically to burn off deposits of coke. This downtime adversely affects production.

Another problem in thermal cracking is the embrittlement of the steel walls in the reaction system. Such embrittlement is due to carburization of the system metallurgy, and ultimately leads to metallurgical failure. In King et al, "The Production of Ethylene by the Decomposition of n-Butane; the Prevention of Carbon Formation by the Use of Chromium Plating", Trans. of the E.I.C., 3, #1, 1 (1959), there is described an application of a $3/1000$ inch thick (3 mil) chromium plate to a stainless steel reactor. This chromium plate is described as peeling-off the surfaces of the steel after a period of several months of operation, which was attributed to the high temperatures required for the reaction, and periodic heating and cooling. This peeling occurred in the absence of steam, which we have found can itself induce peeling under certain process conditions.

Although coking is a problem which must be addressed in process plants such as ethylene crackers and styrene plants, this problem is significantly aggravated in the absence of steam in reactor feedstreams. In fact, it is believed that in the absence of steam, active metal particulates in coke particles will metastasize coke generally throughout the system. That is, the active metal particulates actually induce coke formation on themselves and anywhere that the particles accumulate in the system resulting in coke plugs and hot regions of exothermic reactions. As a result, a premature coke-plugging of the reactor system occurs which can lead to a premature shut-down of the system.

Still another problem in processes that utilize steam, such as thermal cracking, is reduced hydrocarbon throughput. Although steam provides some of the thermal energy required for the cracking reaction, its presence in the cracking tubes necessarily displaces hydrocarbons. Often the amount of steam used is more than necessary to provide the needed thermal energy. If hydrocarbons could replace part or all of the reactor volume that is filled with process steam, hydrocarbon throughput could be increased. Thus, if a unit is not operating at or near the effective steam burner capacity, then less steam at a higher temperature could be used and product production could be increased.

Operating at lower steam levels would have other advantages. For example in ethylene plants, the production of light gases, such as CO and $CO_2$ that have to be scrubbed from the product, would be reduced.

Another process that uses steam is the catalytic dehydrogenation of styrene from ethylbenzene. This process is generally catalyzed with an $Fe_2O_3$ catalyst containing stabilizers and coke retardants. There are two major types of ethylbenzene to styrene processes: isothermal (older technology) and adiabatic. The isothermal process uses a fixed bed, shell and tube heat exchanger. The process runs at about 600° C. outlet temperatures. The steam/hydrocarbon mole ratio is about 8:1 for newer plants and about 10:1 for old plants.

Steam is added to the ethylbenzene/styrene process for at least the following reasons:
  to prevent coking and carburization of the metal surfaces
  to provide heat to the endothermic dehydrogenation reaction
  to inhibit catalyst coking and lengthen catalyst life
  to reduce hydrocarbon partial pressure and shift equilibrium towards styrene However, there are problems with current styrene operations. These include high energy costs associated with heating and cooling steam which result in a high cost of styrene production. A larger plant (per pound of styrene produced) is required to process steam; larger reactors, transfer piping, heat exchangers, etc. are required in the reactor section to handle the large volume of steam. In addition, water separation facilities are required to handle condensed steam downstream of the reactor section.

Another problem is coking in the feed/effluent heat exchanger in styrene plants. Ethylbenzene and steam are heated on the shell side of this exchanger. Coke builds up during normal operation and will eventually damage the exchanger. Premature steam loss (e.g., during a shutdown) initiates massive coke formation that can rapidly destroy the exchanger.

Still another problem is that ethylbenzene and styrene crack in the hot section of the plant to form undesirable by-products, which result in lower selectivity. These cracking reactions are believed to be both thermal and catalytic. Metal-catalyzed reactions on the metal surfaces of the reactor cause at least some of this cracking.

Consequently, there remains a need in the art for improved processes which utilize steam at elevated temperatures and where cracking and coking are reduced, especially at low steam levels. Such a method would include means for inhibiting the undesirable catalytic activity which causes catalytic cracking and coking, as well as means for inhibiting carburization of system metallurgy.

Thus, although there are problems and disadvantage associated with the use of steam, it is currently not possible to remove or reduce the amount of steam from the processes described above. That is, it was not possible to remove or reduce the amount of steam until the discovery of the present invention.

Accordingly, one object of the present invention is to reduce the amount of steam used in hydrocarbon conversion process which currently utilize steam. Another object is to increase the hydrocarbon throughput in these processes. These and other objects will be evident from the description of the invention which follows.

SUMMARY OF THE INVENTION

In one embodiment the invention is an improved hydrocarbon conversion process, comprising a) applying a plating, cladding, paint or other coating to at least a portion of a hydrocarbon conversion reactor system which is used to convert hydrocarbons to products in the presence of steam said coating being effective to reduce the amount of undesirable by-products in said process; and b) operating the hydrocarbon conversion process at a steam to hydrocarbon ratio that is lower than the steam to hydrocarbon ratio at which said process was operated prior to applying said coating. The steam to hydrocarbon ratio is at least 5% lower, preferably at least 10% lower, more preferably at least 50% lower, and most preferably at least 75% lower than prior to applying the coating. The applied plating, cladding, paint or other coating provides a metal passivation layer which reduces catalytic coking and cracking reactions caused by the reactor metallurgy.

In another embodiment the invention is an improved commercial scale hydrocarbon conversion process. The process utilizes steam to dilute the hydrocarbon feed, or to reduce reactant partial pressure, or to provide thermal energy, or to reduce coke deposition. The process comprises applying a metal plating, cladding, paint or other coating to at least a portion of a hydrocarbon conversion reactor system which is used to convert hydrocarbons to products in the presence of steam, optionally forming a bonded metal passivation layer thereon, and converting hydrocarbons in said reactor system at low steam to hydrocarbon ratios.

The coating according to the invention should be applied to those portions of the reactor system which exhibit skin temperatures of at least 1000° F., preferably 1200° F. or more.

In yet another embodiment, the invention is a process for thermally cracking a hydrocarbon feed of ethane, propane and/or naphtha to produce ethylene comprising:
  (i) providing a carburization, abrasion and peeling resistant and coking resistant Group VIB metal protective layer to a steel portion of a cracking reactor system by (a) applying to the steel portion a Group VIB metal plating, cladding or other coating of Group VIB metal effective for forming a carburization resistant protective layer, to a thickness effective to isolate the steel portion from hydrocarbons during operation, and (b) forming the protective layer, anchored to the steel portion through an intermediate carbide-rich bonding layer; and
  (ii) thermally cracking a hydrocarbon feed of ethane, propane and/or naphtha feed to produce ethylene, said process operated at low steam levels to increase hydrocarbon throughput.

The invention can be applied to any hydrocarbon conversion process that uses steam as a diluent or even as a reactant. Such processes include: steam reforming of natural gas (steam to natural gas ratio in primary reformer is about 4–5:1, steam to carbon), production of ethylene and/or propylene by steam cracking(steam to feed ratio ranges from about 0.3 to 1:1 wt/wt), conversion of ethylbenzene to styrene (steam to feed ratio ranges from about 6:1 to 14:1 mole/mole) and, including the SMART™ process (Styrene Monomer Advanced Reheat Technology) and the dehydrogenation of butene to butadiene using steam (steam to butene ratio of about 20:1, mole/mole) or using air/oxygen (steam to butene ratio of about 2 to 4, mole/mole; oxygen to butene ratio about 1:1).

In one preferred embodiment, the invention is applied to an ethylene (steam) cracker. In another preferred embodiment, the invention is applied to the conversion of ethylbenzene to styrene.

Among other factors the invention is based on the discovery that steam to hydrocarbon ratios can be significantly lowered in hydrocarbon conversion process, if a metal passivation layer which reduces hydrocarbon cracking and coking can be provided on a portion, or portions of, the reactor system exposed to hydrocarbons. The effectiveness of metal coatings in preventing catalytic coking at substantially reduced steam levels is unexpected.

While not wishing to be bound by theory, it is believed that steam is needed in current processes, at least in part, to passivate the reactor system metallurgy. The metals of the reactor system are sites for catalysis—such as catalytic coking and cracking—and believed to be a significant source of coke. It is believed that steam converts metallic iron and nickel to their corresponding oxides. While the reduced metals are very active catalysts for coke formation, the oxidized metals are significantly less active. At the same time, the steam can also convert the steel's non-coking metallic chromium to chromium oxide, which is an acidic site for coke production. Similarly, steam can convert aluminum coatings applied to the steel (for example by Alonizing™) to aluminum oxides, which are acidic coking sites.

Since some metals become more active cokers upon treatment with steam and others become less active, it is not at all clear how these factors balance out as a function of the steam to hydrocarbon ratio or as a function of the particular steel used in the reactor system. However, we believe that as steam levels are reduced, the amount of coke formed by typical reactor metallurgies becomes enormous. That is why the processes discussed herein are commercially operated at the currently relatively high steam to hydrocarbon ratios, even given the disadvantages of steam as discussed previously.

Additionally, we believe that the catalytic coke produced by the reactor metallurgy is an opportune site for laying down thermal coke. Indeed, it may be that metallic iron and nickel are such highly active catalysts that they generate "hot spots" at and near the metal site. These hot spots are much hotter than the process temperature or even the reactor wall temperature. This theory is suggested by our observation of molten metal during petrographic analysis of some of our coke samples. The hot spots in turn produce large amounts of thermal coke in the vicinity of the coking catalysts. We now believe that without catalytic coke, thermal coke production is also substantially reduced.

Accordingly, one object of the invention is to provide an improved method of converting hydrocarbons at reduced steam to hydrocarbon ratios, where catalytic cracking and coking by the reactor system is minimized. Preferably carburization is also reduced.

Another object of this invention is to provide a method for inhibiting coking, carburization and metal-dusting in processes which currently utilize steam. The method includes pretreating surfaces exposed to a low steam atmosphere to form a protective layer which is more resistant to coking, embrittlement, carburization and metal-dusting than the materials conventionally used to manufacture the reactor system.

Even another preferred embodiment relates to the discovery that simply providing a protective plating, cladding or other coating such as a paint, to a reactor system will not necessarily be sufficient to completely address the aforementioned problems. Such a protective layer must be of sufficient thickness to provide a complete, uninterrupted coating of the underlying base metal, and it must remain complete over time. Even minor imperfections, pinholes or other flaws in the protective layer can provide destructive carburization sites sufficient to shut-down operation.

As indicated above, the present invention provides a method for inhibiting catalytic coking and carburization in hydrocarbon conversion processes. The method includes pretreating surfaces of the reactor system with a metal coating which inhibits carburization and passivates the catalytic cracking and coking sites under the hydrocarbon conversion process conditions. The hydrocarbon conversion process is then operated at a steam to hydrocarbon ratio that is at least 5% lower, preferably at least 10% lower, more preferably at least 50% lower, and most preferably at least 75% lower than the steam to hydrocarbon ratio at which said process was operated prior to applying said coating. Optionally, or in the alternative, the coating composition also inhibits or reduces carburization and metal-dusting.

Although preferred, reducing steam to hydrocarbon ratios does not necessarily mean that hydrocarbon throughput must be increased. Rather, it may be advantageous to just replace steam with another diluent or heat source. For example, in the absence of steam, oxidation by-products ($CO$, $CO_2$) would be eliminated, simplifying product cleanup. Also, for chromium and aluminum passivation layers, replacing steam with another diluent would minimize the formation of chromium and aluminum oxides which are coke formers. For example, if the steam in an ethylene cracker were replaced with nitrogen or ammonia, non-coking chromium nitrides would be produced on the surface of the chromium passivation layer.

In one embodiment of the invention, it is preferred to reduce the amount of steam added so that it is not more than 150% of the amount needed to heat the feed to the desired process temperature, preferably not more than 110%, and most preferably not more than 105%.

Also, to the extent that the metal passivation technology protects the steel from premature failure via carburization and reduces coking in the furnace tubes, and to the extent that the metal passivation layer is susceptible to steam attack, this attack would be expected to be reduced at lower steam to hydrocarbon ratios. For example, we have found experimentally that chromium or aluminum-coated steels will prevent or at least strongly inhibit coking at temperatures from 1600° F. to 2000° F. Each of the coatings has been found to be attacked by steam under certain conditions with two undesirable results. First, steam causes oxidation of the chromium metal and various carbide and aluminide phases. This oxidation will eventually consume the protective coating. In addition, in the case of chromium, steam can oxidize the carbide glue layer formed between chromium plate and steel, causing the plate to peel. Second, steam produces oxide phases of aluminum or chromium, which can themselves catalyze cracking reactions and produce coke via an acid site mechanism.

Since the metal passivation layer inhibits coking and carburization, the hydrocarbon conversion process may be operated under conditions of low sulfur. For example, the processes can be operated without added sulfur or sulfur compounds. This simplifies processing.

With the foregoing, as well as other objects, advantages, features and aspects of the disclosure that will become hereinafter apparent, the nature of the disclosure may be more clearly understood by reference to the detailed description and the appended claims.

DETAILED DESCRIPTION OF THE INVENTION

As discussed above, it is known that there are many advantages associated with reduced steam to hydrocarbon ratios. It also known that metal protection layers can reduce or prevent carburization and coking. However, no one has previously operated metal-coated reactor systems at reduced steam to hydrocarbon ratios. Indeed, those skilled in the art were unwilling to even consider this combination, as it was believed to be totally unpredictable how effective the combination would be, and the result could be catastrophic. Moreover, it was not clear that one could achieve so great an improvement in catalytic cracking and coking at reduced steam levels merely by applying a thin metallic coating to reactor system surfaces. Thus, although the desirability of reducing steam levels was known, it was surprising that the metal passivated reactor systems could operate at substantially reduced steam to hydrocarbon ratios for extended periods of time without excessive coking.

Although the terms "comprises" or "comprising" are used throughout this specification, these terms are intended to encompass both the terms "consisting essentially of", and "consisting of" in various preferred aspects and embodiments of the present invention.

The term "reactor system" as used herein refers to an apparatus or portion thereof wherein hydrocarbon feeds are contacted at elevated temperatures to produce products. The reactor system has one or more hydrocarbon conversion reactors, their associated piping, heat exchangers, furnace tubes, etc. In one embodiment, the reactor system is at least one cracking furnace, including any cracking or furnace tubes thereof, effective to crack a feed material into desired products such as ethylene. In another embodiment, the reactor system is at least one dehydrogenation reactor, including any furnace tubes thereof, effective to dehydrogenate ethylbenzene into styrene. Among other configurations, such a reactor may include furnace tube reactors with or without catalyst, or shell and tube heat exchangers used as reactors. In another embodiment, the reactor system is a steam reformer.

As used herein, the term "metal-containing coating" or "coating" is intended to include claddings, platings, paints and other coatings which contain either elemental metals, metal oxides, organometallic compounds, metal alloys, mixtures of these components and the like. The metal(s) or metal compounds are preferably a key component(s) of the coating. Flowable paints that can be sprayed or brushed are a preferred type of coating.

As used herein, the term "metal-coated reactor system" is intended to include reactor systems (see above) having a metallic coat, cladding, plating, or paint applied to at least a portion (preferably at least 50%, more preferably at least 75%) of the surface area that is to be contacted with hydrocarbons at process temperature. This metal-coated reactor system comprises a base metal or material (such as carbon, chrome, or stainless steel) having one or more adherent metallic layers attached thereto.

By "low steam", or "low steam levels" or "low steam atmosphere", there is intended steam levels below those conventionally used in commercial processes. This depends on the particular process, and often on the hydrocarbon feed, as discussed below.

Platings, Claddings, Paints and Other Coatings

A variety of coatings may be used to passivate the reactor metallurgy, thus reducing its ability to catalyze cracking and coking reactions. The coating is selected so that the selectivity to desired product in the hydrocarbon conversion process at the reduced steam level is acceptable under the reaction conditions, i.e, so that the process is economic. The choice of coating varies with the hydrocarbon conversion process and its process conditions. Coating materials are selected so the formed metal passivation layer is stable under the process conditions. Effective coatings are those that reduce the volume or weight percent of undesirable by-products formed, at a constant hydrocarbon to steam ratio, relative to the uncoated steel surface. These coatings can be identified by a simple test where coupons of coated and uncoated materials are compared under identical, simulated process conditions.

Preferred metals that may be used in the process of this invention are selected from the group consisting of tin, antimony, germanium, arsenic, aluminum, gallium, indium, copper, and mixtures, intermetallic compounds and alloys thereof. The metal can be bonded to the steel using a second metal as a binder, for example, copper is preferably bonded to the steel using a tin layer as a binder, as known in the art. Other useful metals are Group VIB metals (including chromium, molybdenum and tungsten), silicon, titanium, niobium, zirconium, tantalum and hafnium. Bismuth, indium and lead are also useful, especially when applied to steels that are very rich in nickel. More preferred metals are selected from the group consisting of tin, antimony, chromium and aluminum.

Not all metal-containing platings, claddings, paints and other coatings are useful in this invention. Especially preferred metals are those that interact with, and preferably react with, the base material of the reactor system at temperatures below or at the intended hydrocarbon conversion conditions to produce an adherent metallic layer. The preferred metal depends on the hydrocarbon conversion process of interest, its temperature, reactants, etc.

Metals that are mobile or melt below or at the process conditions are especially preferred. Reducible metal oxides and low melting metal compounds are also preferred. These include those selected from among tin, antimony, germanium, arsenic, bismuth, gallium, indium, copper, lead and mixtures, intermetallic compounds and alloys thereof. Preferred metal-containing coatings are selected from the group consisting of tin, antimony, germanium, bismuth, aluminum, and mixtures, intermetallic compounds and alloys thereof. Especially preferred coatings include tin-, antimony-and germanium-containing coatings. These coatings all form continuous and adherent protective layers. Tin coatings are especially preferred—they are easy to apply to steel, are inexpensive and are environmentally benign.

In some instances applying a coating of the aforementioned elements as metals or reducible oxides, will not be particularly preferred. That is because, to provide a good reactive coating it is necessary that the material be molten. Unfortunately, some metals such as germanium, and to some extent antimony, have melting points which exceed levels which are practical, or even attainable, with a particular piece of equipment or apparatus. In those instances it is desirable to use compounds of those elements which have lower melting points.

For example, sulfides of antimony and germanium have lower melting points than their respective metals and can be used to produce antimonide and germanide coatings on steels in a hydrogen-rich, or perhaps even a non-reducing, atmosphere. Such sulfides can be used in the form of powders or paints which react to produce antimonide and germanide coatings at significantly lower temperatures than those required for the metals. Tests have shown that antimonide coatings can be applied to 300 series stainless steel and Incoloy® 800 using $Sb_2S_3$ powder at 1030° F. in 20 hours of curing under an atmosphere of 7% $C_3H_8$ in $H_2$. Also, tests have shown that germanide coatings can be applied to Incoloy® 800 using $GeS_2$ powder at 1150° F. under the same conditions.

A coating of antimony applied to iron bearing steels protects these steels from carburization, coking and metal dusting under low temperature cracking conditions. In fact, an antimony paint applied to iron bearing steels will provide protection against carburization, catalytic coking, and metal dusting at 1600° F.

Metal-containing coatings that are less useful include certain metal oxides such as molybdenum oxide, tungsten oxide and chromium oxides. In part this is because it is difficult to form adherent metallic protective layers from these oxides using hydrogen at most hydrocarbon processing conditions.

Metal-containing coatings can be applied in a variety of ways, which are well known in the art, such as electroplating, chemical vapor deposition, and sputtering, to name just a few. Preferred methods of applying coatings include painting and plating. Where practical, it is preferred that the coating be applied in a paint-like formulation (hereinafter "paint"). Such a paint can be sprayed, brushed, pigged, etc. on reactor system surfaces.

One preferred protective layer is prepared from a metal-containing paint. Preferably, the paint is a decomposable, reactive, metal-containing paint which produces a reactive metal which interacts with the steel. Tin is a preferred metal and is exemplified herein; disclosures herein about tin are generally applicable to other reducible metals such as germanium. Preferred paints comprise a metal component selected from the group consisting of: a hydrogen decomposable metal compound such as an organometallic compound, finely divided metal and a metal oxide, preferably a reducible metal oxide.

It is preferred that the coatings be sufficiently thick that they completely cover the base metallurgy and that the resulting protective layers remain intact over years of operation. This thickness depends on the intended use conditions and the coating metal. For example, tin paints may be applied to a (wet) thickness of between 1 to 6 mils, preferably between about 2 to 4 mils. In general, the thickness after curing is preferably between about 0.1 to 50 mils, more preferably between about 0.5 to 10 mils.

Some preferred coatings are described in WO 92/15653 to Heyse et al., corresponding to U.S. Ser. No. 803,063, which is incorporated herein by reference in its entirety. This application also describes some preferred paint formulations. One especially preferred tin paint contains at least four components or their functional equivalents: (i) a hydrogen decomposable tin compound, (ii) a solvent system, (iii) finely divided tin metal and (iv) tin oxide. As the hydrogen decomposable tin compound, organometallic compounds such as tin octanoate or neodecanoate are particularly useful. Component (iv), the tin oxide is a porous tin-containing compound which can sponge-up the organometallic tin compound, and can be reduced to metallic tin. The paints preferably contain finely divided solids to minimize settling. Finely divided tin metal, component (iii) above, is also added to insure that metallic tin is available to react with the surface to be coated at as low a temperature as possible. The particle size of the tin is preferably small, for example one to five microns. Tin forms metallic stannides (e.g., iron stannides and nickel/iron stannides) when heated in streams containing hydrogen and hydrocarbons.

In one embodiment, there can be used a tin paint containing stannic oxide, tin metal powder, isopropyl alcohol and 20% Tin Ten-Cem (manufactured by Mooney Chemical Inc., Cleveland, Ohio). Twenty percent Tin Ten-Cem contains 20% tin as stannous octanoate in octanoic acid or stannous neodecanoate in neodecanoic acid. When tin paints are applied at appropriate thicknesses, typical reactor start-up conditions will result in tin migrating to cover small regions (e.g., welds) which were not painted. This will completely coat the base metal. Preferred tin paints form strong adherent protective layers early during the start-up process.

At extremely low steam levels, iron bearing reactive paints are also useful in the present invention. A preferred iron bearing reactive paint will contain various tin compounds to which iron has been added in amounts up to one third Fe/Sn by weight. The addition of iron can, for example, be in the form of $Fe_2O_3$. The addition of iron to a tin containing paint should afford noteworthy advantages at extremely low steam levels; in particular: (i) it should facilitate the reaction of the paint to form iron stannides thereby acting as a flux; (ii) it should dilute the nickel concentration in the stannide layer thereby providing better protection against coking; and (iii) it should result in a paint which affords the anti-coking protection of iron stannides even if the underlying surface does not react well.

A preferred embodiment of the invention uses a reactor system including a stainless steel portion, which comprises providing the stainless steel portion with a stannide protective layer of sufficient thickness to isolate the stainless steel portion from hydrocarbons, which protective layer is anchored to the steel substrate through an intermediate carbide-rich, nickel-depleted stainless steel bonding layer. More particularly, the stannide layer is nickel-enriched and comprises carbide inclusions, while the intermediate carbide-rich, nickel-depleted bonding layer comprises stannide inclusions. More preferably the carbide inclusions are continuous as they extend, substantially without interruption, from the intermediate carbide-rich, nickel-depleted bonding layer into the stannide phase, and the stannide inclusions are likewise continuous extending from the stannide layer into the intermediate carbide-rich, nickel-depleted bonding layer. The interface between the intermediate carbide-rich, nickel-depleted bonding layer and the nickel-enriched stannide layer is irregular, but is otherwise substantially without interruption. The extent to which the aforementioned phases, layers and inclusions develop are a function of the reducing conditions and temperature at which the initial plating, cladding or other coating is treated, and the amount of time at which exposure is maintained.

If steel stress relief techniques are used when assembling a reactor system, the production of iron oxides prior to application of the resistant plating, cladding or coating should be minimized. This can be accomplished by using a nitrogen atmosphere during steel stress relief (e.g., at 1650° F.).

An effective protective layer preferably resists deleterious chemical alteration, as well as peeling. Additionally, the protective layer must maintain its integrity through operation. As such, the protective coating must be sufficiently abrasion resistant during start-up and operation. Metallic chromium-based coatings have these advantages.

A preferred embodiment of this invention uses a chromium protective layer. Preferably, the chromium layer is applied by a plating process such as electroplating, followed by curing. It can also be applied as a reducible paint which upon curing in a $H_2$-rich (or pure) environment, in the absence of steam, forms a continuous chromium metal layer of substantial thickness, indistinguishable from electroplated material, except that it is virtually free of cracks. Such a paint may be prepared from chromium III chloride and petroleum jelly. The resulting protective layer is very finely and cleanly anchored to the underlying steel through a carbide-rich bonding layer. Chromium paint protection can be applied and cured in-situ to an existing plant.

Cracks have been observed to form in chromium protective layers, especially after the initial heating of an electroplated material. These cracks can allow steam (which is typically present) to attack the steel/chromium interface and undermine the chromium protective layer. According to another embodiment of the invention there is provided a novel procedure which includes a step of treating a chromium coated surface with hydrocarbons in the absence of steam which produces a metal carbide filler of the cracks which effectively seals-off the chromium coating and carbide-rich bonding layer from steam attack.

In yet another embodiment of the invention, a protective layer is formed by bonding a chromium layer to steel in the presence of a nitrogen-containing compound at elevated temperature. This has the advantage of forming not only a carbide-rich bonding layer, but also results in the filling of cracks in the chromium layer with chromium nitride which effectively seals off the carbide-rich bonding layer from steam attack.

While not wishing to be bound by theory, it is believed that the suitability of various materials can be selected and classified according to their responses to carburizing atmospheres. For example, iron, cobalt, and nickel form relatively unstable carbides which will subsequently carburize, coke and dust. Elements such as chromium, niobium, vanadium, tungsten, molybdenum, tantalum and zirconium, will form stable carbides which are not subject to dusting and coking. Elements such as tin, antimony, germanium and bismuth do not form carbides or coke. And, these compounds can form stable compounds with many metals such as iron, nickel and copper under hydrocarbon conversion conditions. Stannides, antimonides and bismuthides, and compounds of lead, mercury, arsenic, germanium, indium, tellurium, selenium, thallium, sulfur and oxygen are also resistant.

A final category of materials include elements such as silver, copper, gold, platinum and refractory oxides such as silica and alumina. These materials are resistant and do not form carbides, or react with other metals in a coking and carburizing environment under hydrocarbon conversion conditions.

Because different areas of the reactor system of the invention can be exposed to a wide range of temperatures, the material selection can be staged, such that those materials providing protective layers with better coking passivation and carburization resistance are used in those areas of the system experiencing the highest temperatures.

With regard to materials selection, it was discovered that oxidized Group VIII metal surfaces such as iron, nickel and cobalt are more active in terms of coking and carburization than their unoxidized counterparts when used in a reducing environment. For example, it was found that after reduction an air roasted sample of 347 stainless steel was significantly more active than an unoxidized sample of the same steel. This is believed to be due to a re-reduction of oxidized steels which produces very fine-grained iron and/or nickel metals. Such metals are especially active for carburization and coking.

In one embodiment, aluminum passivation layers are used in this invention. Aluminized materials have been commercially tested in ethylene steam crackers. However, such processes have been operated at conventional high steam to hydrocarbon ratios. These tests were apparently only partially successful, and interest in these materials has waned. Surprisingly, we have now discovered that these materials are more effective in resisting coking at low steam to hydrocarbon ratios, e.g, at ratios well below those used in conventional ethylene cracking processes.

The application of thin aluminum films to metal surfaces of the reactor system or the use of aluminized materials, such as Alonized™ steels during construction, can provide surfaces which are sufficiently resistant to coking and carburization under low steam conditions. Such materials may be applied to at least a portion of the metal surfaces in the reactor system. Such metal surfaces include but are not limited to, the reactor walls, furnace tubes, and furnace liners.

Suitable methods for applying aluminum to metal surfaces such as steels include well known deposition techniques. Preferred processes include powder and vapor diffusion processes such as the "Alonizing" process, which has been commercialized by Alon Processing, Inc., Tarentum, Pa. Essentially, "Alonizing" is a high temperature diffusion process which alloys aluminum into the surface of a treated metal, such as steel—producing aluminides. In this process, the steel is positioned in a retort and surrounded with a mixture of blended aluminum powders. The retort is then hermetically sealed and placed in an atmosphere-controlled furnace. At elevated temperatures, the aluminum deeply diffuses into the treated metal resulting in an alloy. After furnace cooling, the substrate is taken out of the retort and excess powder is removed. Straightening, trimming, beveling and other secondary operations can then be performed as required. This process can render the treated ("alonized") metal resistant to carburization and metal dusting under low-steam hydrocarbon conversion conditions according to the invention.

A coating of bismuth applied to very nickel rich steel alloys (e.g., Inconel® 600) can protect those steels against carburization, catalytic coking, and metal dusting under cracking conditions. This has been demonstrated at temperatures of up to 1600° F. Bismuth coatings may also be applied to iron bearing steels and provide protection against carburization, metal dusting, and catalytic coking under cracking conditions. Also, a metal coating comprising a combination of bismuth, antimony, and/or tin can be used.

Cure Process Conditions

Although not necessary for all coating materials, for some coatings it is preferred that the coating be cured prior to use. This is especially true for coating materials containing reducible metal oxides and organometallic components, such as oxygen-containing organometallic compounds.

In a preferred embodiment, cure conditions comprise a heating step and optionally a reducing step. Here coated materials are cured in a hydrogen-containing atmosphere at elevated temperatures. Hydrogen contacting preferably occurs while the protective layer is being formed. In general, the contacting of the reactor system having a metal-containing coating, plating, cladding, paint or other coating applied to a portion thereof with a hydrogen-containing gas is done for a time and at a temperature sufficient to produce a metallic protective layer. These conditions may be readily determined. For example, coated coupons may be heated in the presence of hydrogen in a simple test apparatus; the formation of a continuous passivation layer may be determined using petrographic analysis.

The resulting protective layer is able to withstand repeated temperature cycling, and does not degrade in the reaction environment. Preferred protective layers are also useful in oxidizing environments, such as those associated with coke burn-off. In a preferred embodiment the cure step produces a metallic protective layer bonded to the steel through an intermediate bonding layer, for example a carbide-rich bonding layer as described in WO 94/15898.

Cure conditions depend on the coating metal and are selected so they produce a continuous and uninterrupted protective layer which adheres to the steel substrate. Gas flow rates and contacting time depend on the cure temperature, the coating metal and the components of the coating composition. Cure conditions may also depend on the hydrocarbon conversion process to which the invention is applied. For example, it is preferred that cure temperatures are similar to the hydrocarbon conversion conditions to which the reactor system will be applied.

It is preferred that cure conditions result in a passivation layer that is firmly bonded to the steel. This may be accomplished, for example, by curing the applied coating at elevated temperatures. As discussed above, metal or metal compounds contained in the paint, plating, cladding or other coating are preferably cured under conditions which produce molten and/or mobile metals and/or compounds. Thus, paints containing germanium and antimony compounds are preferably cured between 1000° F. and 1400° F. Tin paints are preferably cured between 900° F. and 1100° F. Curing is preferably done over a period of hours, often with temperatures increasing over time.

As an example of a suitable paint cure for a tin paint, the system including painted portions can be pressurized with flowing nitrogen, followed by the addition of a hydrogen-containing stream. The reactor inlet temperature can be raised to 800° F. at a rate of 50–100° F./hr. Thereafter the temperature can be raised to a level of 950–975° F. at a rate of 50° F./hr, and held within that range for about 48 hours.

A preferred method of coating an existing or new reactor surface is to decompose an organometallic compound in a hydrogen atmosphere at elevated temperature. For organo-tin compounds at temperatures of about 900° F., this produces reactive metallic tin on the reactor surface. which tin will further react with the surface metal to passivate it.

Optimum coating temperatures will depend on the particular organometallic compound, or the mixtures of compounds if alloys are desired. Typically, an excess of the organometallic coating agent can be pulsed into the reactor at a high hydrogen flow rate so as to carry the coating agent throughout the system in a mist. The flow rate can then be reduced to permit the coating metal mist to coat and react with the reactor surface. Alternatively, the compound can be introduced as a vapor which decomposes and reacts with the hot walls of the reactor in a reducing atmosphere.

Depending on the components of the metal-containing coating, reaction of the reactor system metallurgy with the coating can occur. Preferably, the reaction results in an intermediate carbide-rich bonding or "glue" layer that is anchored to the steel and does not readily peel or flake. For example, metallic tin, germanium and antimony (whether applied directly as a cladding or produced in-situ) readily react with steel at elevated temperatures to form a bonding layer as is described in WO 94/15898 or WO 94/15896, both to Heyse et al.

For chromium coatings, such as chromium plate, it is preferred to cure in nitrogen, so cracks in the plate will be filled with chromium nitrides.

The Base Construction Material

There are a wide variety of base construction materials to which the process of this invention may be applied. In particular, a wide range of steels may be used in the reactor system. In general, steels are chosen so they meet minimum strength and flexibility requirements needed for the intended hydrocarbon conversion process. These requirements in turn depend on process conditions, such as operating temperatures and pressures.

Useful steels include carbon steel; low alloy steels such as 1.25, 2.5, 5, 7, and 9 chrome steel; stainless steels including the 300 series which includes the 304, 316 and 347, the 400 series such as 446; heat resistant steels including HK-40 and HP-50, high nickel steels such as Incology® 800, as well as treated steels such as aluminized or chromized steels. Very nickel-rich steels, i.e., containing >50% nickel, preferably >70% nickel, such as Inconel® 600 which is 75% nickel, can also be used. Heat resistant steels such as HK-40 and HP-50 are especially preferred in ethylene crackers using chromium coatings. These steels apparently do not lose their passivation layer through diffusion of the chromium into the steel.

In a preferred embodiment, the process of the invention has the metal-containing plating, cladding, paint or other coating is applied to at least one surface of a furnace tube, more preferably a gas-fired furnace tube.

Hydrocarbon Processing

The invention will be described hereinbelow in terms of the thermal cracking of a hydrocarbon feed to produce ethylene. However, the various aspects of the invention are not intended to be limited to that embodiment. As will be apparent to those skilled in the art, they are useful in other areas of high temperature hydrocarbon processing such as both thermal and catalytic conversions of a variety of hydrocarbon feeds to produce a variety of desired products. Thus, the invention is applicable not only to ethylene crackers and their furnace tubes but also to other furnaces and furnace tubes which are exposed to either carburizing or coking environments at high temperature, such as steam reforming of hydrocarbons and the thermal cracking of hydrocarbons to produce propylene.

Also, while the invention is described in terms of using chromium to produce a protective layer, molybdenum, tungsten, and mixtures thereof, with or without the use of chromium, may be used as well. Additionally, aluminum protective layers may also be used alone or in combination with other metals.

In one preferred embodiment, the invention is directed to a method of protecting an ethylene cracker furnace tube that is to be contacted with steam and hydrocarbons at temperatures above about 1600° F. The method comprising providing a coke-resistant chromium protective layer to an ethylene cracker tube by applying a chromium layer to at least a portion of the inner surface of a ethylene cracker tube which is made of a heat-resistant steel, and forming a metallic chromium protective layer, anchored to the steel portion through a continuous intermediate carbide-rich bonding layer. The thickness of the chromium layer is effective to substantially isolate the iron and nickel in the steel portion from hydrocarbons during operation. The bonding layer is preferably formed by heating the applied chromium layer under conditions which prevent formation of chromium oxides.

The chromium protective layer according to the invention can be applied as a plating, cladding or other coating such as chromium-containing paint or by chemical vapor deposition. Then the plating, cladding or other coating is treated in a manner effective to form a protective layer which is anchored to the steel substrate through a continuous and uninterrupted carbide-rich bonding layer, thereby providing the necessary abrasion resistance and resistance to peeling. Preferably, the plating, cladding, or coating is resistant to abrasion, peeling or flaking for a period of 1 year, preferably 2 years, and more preferably 3 years such that the reactor system will maintain its coking passivation carburization resistant properties without reapplication.

The thickness of the chromium layer after application should be between 0.5 and 15 mils, preferably 1 and 10 mils (25 and 250 microns), and more preferably between 2 and 8 mils.

It has been observed that the high operating temperatures used in steam cracking (1750–1850° F.) stabilize chromium carbides and nitrides relative to chromium oxides. Conversely, at temperatures lower than about 1600° F., chromium oxides are stabilized relative to chromium carbides and nitrides. Therefore, it is preferable to maintain the protective layer-coated steel at high temperatures so that chromium oxides will not replace chromium carbides and nitrides, and the carbide-rich bonding layer will remain protected from steam attack over time. It is further preferred that the protective layer-coated steel is brought to high temperatures before adding steam, or that steam addition is minimized, preferably avoided, during curing.

According to a preferred embodiment of a thermal cracking operation of the present invention, a diluent fluid comprising steam is combined with a hydrocarbon feed such as ethane and/or propane and/or naphtha, and introduced into a cracking furnace having a metal passivation layer applied thereto. Within the furnace, the feed stream which has been combined with the diluent fluid which comprises low steam levels will be converted to a gaseous mixture which primarily contains hydrogen, methane, ethylene, propylene, butadiene, and small amounts of heavier gases. At the furnace exit this mixture will be cooled to remove most of the heavier gases, and then compressed. The compressed mixture can then be routed through various distillation columns where the individual components such as ethylene are separated and purified.

The cracking furnace may be operated at any suitable temperature or pressure. For example, in the process of steam cracking of light hydrocarbons to ethylene, the temperature of the fluid flowing through the cracking tubes increases during processing and will attain a temperature of about 1575° F. The wall temperatures of the cracking tubes will be even higher. Furnace temperatures of nearly 2100° F. may be reached. Typical pressures for a cracking operation will generally be in the range of about 5 to about 20 psig at the outlet of the cracking tube.

For ethylene crackers, the passivation layer according to this invention should be applied to those portions of the reactor system which exhibit skin temperatures of at least 1200° F., preferably at least 1500° F., and most preferably at least 17000° F., during operation. The higher the temperature, the more important it is to apply a passivation layer.

One advantage of the present process is that it can be operated with less steam. Steam is traditionally added to olefin crackers. In part it is added to passivate the coking and carburization tendency of the steel. At lower steam levels, the steel becomes carburized and embrittled relatively rapidly, leading to premature failure. Using the current invention, less steam can be used, for example, to increase hydrocarbon throughput.

Generally, steam levels in ethylene plants vary in concert with feed rates to maintain a constant steam to feed ratio. Different steam to hydrocarbon ratios are used with different feeds: e.g., with ethane/propane mixtures the weight ratio is between 0.3 and 1; with light naphtha the ratio is between 0.5 and 1; and with heavier feeds the ratio is 0.6 to 1 and higher. In part, the steam protects the steel from excess heat.

The invention, as applied to ethylene crackers reduces the steam to hydrocarbon (wt/wt) ratio below current commercial operation (0.30). Thus, in the presence of a passivation layer, the steam to hydrocarbon ratio is preferably between 0.25 to 0.01, more preferably below 0.20 and most preferably below 0.10 for ethane and propane feeds or mixtures thereof.

For heavier feeds, the steam to hydrocarbon ratio is reduced in a similar manner. Thus for naphtha it is preferably between 0.42 to 0.01, more preferably below 0.33 and most preferably below 0.17. For gas oil feed, the ratio is preferably below 0.5, more preferably below 0.4 and most preferably below 0.3.

In general, it is not preferred to totally eliminate the steam without adding another diluent. The diluent can include hydrogen, nitrogen, ammonia, etc.

In another embodiment, the invention is applied to the production of styrene. The dominant process for styrene production is adiabatic or isothermal ethylbenzene dehydrogenation. Currently plants that convert enthylbeneze to styrene operate at the following conditions:

|  | adiabatic | isothermal |
| --- | --- | --- |
| Temperature, ° C. | 550–660 | 540–600 |
| Pressure, psia | 6–14 | 7–15 |
| WHSV, lb/lb/hr | 0.3–0.5 | 0.5–0.7 |
| Steam/EB, wt/wt | 1.2–1.8 | 0.6–0.9 |

The steam to ethylbenzene ratio is routinely monitored, typically by controlling and recording the flow rate of steam and ethylbenzene to the dehydrogenation reactors.

Commercial ethylbenzene dehydrogenation catalysts require steam to maintain the catalyst in proper active state, and to reduce coke deposition on the catalyst. One current commercial catalyst comprises iron oxide and an alkali compound. Iron oxide catalyzes the ethylbenzene dehydrogenation reaction. In the absence of steam, iron oxide would likely reduce to elemental iron which is not a dehydrogenation catalyst. The reaction of steam with carbon (coke) is promoted by alkali compounds. Without steam, coke deposits on the catalyst and causes catalyst deactivation.

New catalysts are being developed which are capable of running at low steam to ethylbenzene ratios without severe deactivation. However, none of these catalysts have yet been commercialized, perhaps because they exhibit low selectivity in processes using conventional reactor metallurgy. At low steam to ethylbenzene ratios, non-selective reactions catalyzed by the metal surfaces of the reactor section become significant. The present invention allows styrene plants to run at low steam to ethylbenzene ratios, preferably without losing any selectivity. The new catalysts will be especially useful in plants having coated reactor systems.

When operating at lower steam to hydrocarbon ratios, it is important to choose catalysts that do not coke at these conditions. To accomplish this, coke inhibitors such as alkali metal and alkaline earth metal oxides (e.g., $K_2O$, KOCH, $K_2CO_3$, MgO, BaO, LiOH) may be added to the dehydrogenation metal catalyst. Also, the metal component of the dehydrogenation catalyst may be passivated, for example by reaction with sulfur, tin, antimony or bismuth.

Advantages for reducing the steam to ethylbenzene ratio in styrene plants are:

higher production rates, increased hydrocarbon throughput lower energy costs lower pressure drop across the catalyst bed lower capital costs Steam lowers plant capacity by limiting the amount of reactant (ethylbenzene) able to flow through the reactor section of the plant. By reducing the amount of steam passing through a styrene plant, styrene production can be increased.

High energy costs associated with heating and cooling steam results in a high cost of styrene production. Also, diluents, such as steam, cause a high pressure drop across the reactors. A high pressure drop increases operating costs and decreases conversion.

Steam and ethylbenzene are heated in separate equipment. Steam is heated in a gas-fired furnace, while ethylbenzene is heated in heat exchangers. In addition, separation facilities are required to separate condensed steam from other reactor products. Additional equipment increases capital costs and decreases operation flexibility.

Although a variety of coatings may be used in styrene plants, the following coatings are preferred: aluminum, antimony, chromium, tin, and mixtures, intermetallic compounds and alloys thereof. Bismuth, lead and indium coatings may be used in plants where the base construction material is a very nickel-rich steel such as Inconel® 600, which contains about 75% nickel.

The examples (below) show that substantially improved selectivities are observed with a metal passivated reactor system, probably due to less catalytic cracking and coking. These improved selectivities allow for reductions in the steam to hydrocarbon ratio, which increase production. The results are much better than would have been predicted, based on what is known about the reactivities of the different metals and metal oxides of the reactor system. Indeed, it was unexpected that so great a reduction in coke production would occur that one could substantially reduce the steam to hydrocarbon.

When a styrene plants has been coated with one of the above-described coatings, the plant may be operated at a steam to ethylbenzene (wt) ratio between 0.6 and about 0.01, preferably between 0.4 and about 0.01, more preferable between 0.2 and about 0.01, and most preferably as low as about 0.01.

In another embodiment, the invention is applied to steam-methane reforming. Steam is an integral part of the steam reforming process and cannot be removed completely. Nevertheless, the industry trend is toward reduced steam levels to increase methane throughput. A penalty associated with reduced steam is lower product hydrogen purity, but new plants are equipped to purify the hydrogen. Lower steam levels would cause increased CO and $CO_2$ make, and could possible threaten the metallurgy (Nb-HP-50) by carburization attack and embrittlement. The process runs at about 1600° F. (ultimately), with a tube wall temperature of 1750°–1800° F. For steam reformers, chromium and possibly aluminide coatings are preferred.

Some older plants, mainly in Middle East, run on heavier, naphtha feeds. In these, steam levels are kept higher than in those plants that run mainly on methane. This appears to be because of coking, perhaps on the catalyst (NiO) but probably also on the tube walls. Less steam and a coated reactor system could be used with these heavier feeds, but the catalyst would probably be replaced with one that does not coke at the lower steam to carbon ratios.

Current steam levels range from 3 to 5 (steam to carbon). Newer plants with light feed run at 3. Using a metal passivated reactor system, we envision operating at steam to carbon ratios of about 2.5, preferably about 2; more preferably about 1.

To obtain a more complete understanding of the present invention, the following examples illustrating certain aspects of the invention are set forth. It should be understood, however, that the invention is not intended to be limited in any way to the specific details of the examples.

EXAMPLE 1

Dry carburization tests were run using 7% $C_3H_8$ in $H_2$ over HP-50 steel chips in a Lindberg Quartz tube furnace. The results were:

|  | Cr "Paint"* on HP50 | Cr Plate** on HP50 | Untreated HP50 |
|---|---|---|---|
| 1600° F. 4 Hrs | Trace of coke Uncarburized | Essentially coke free Uncarburized | Coked Carburized |
| 2000° F. 2 Hrs | Trace of coke Uncarburized | Substantially coke free Uncarburized | Coked Carburized |

*$CrCl_2$ powder on HP-50 reduced 2 hrs. at 1500° F. in $H_2$
**Commercial hard Cr plate on HP-50 heat treated in $H_2$ at 1500° F. for 2 hrs.

Microscopic analysis revealed a chromium-carbide bonding layer between the chromium coatings and the underlying steel in the chromium-treated samples. The untreated HP-50 showed deep and intense carburization.

EXAMPLE 2

Wet coking and carburization tests were run using 7% $C_3H_8$ in $H_2$ bubbled through water in a Lindberg Quartz tube furnace. The tests were done over Cr-plated steel. The results were:

|  | Cr Plate** on HP50 | Untreated HP50 |
|---|---|---|
| 1600° F. 4 Hrs | Coke free Uncarburized | Coked Lightly carburized |
| 2000° F. 2 Hrs | Essentially coke free Uncarburized | Coked Lightly carburized |

This example shows that, compared to Example 1, steam inhibits carburization. Microscopic analysis of the chromium-treated steel after the tests revealed a chromium-carbide bonding layer between the chromium metal coating and the underlying steel in the chromium-treated sample. This layer was thicker in the higher temperature experiment. Some chromium oxide was observed on the exterior surface and within the natural cracks of the chromium plate.

EXAMPLE 3

A Chromium Plated HP-50 Steel

A section of a furnace tube made of HP-50 Steel was cleaned and then electroplated to produce a hard chromium coating. The thickness of the coating was between 75 and 100 microns. This section was welded into the furnace tube in an ethylene cracking unit.

After cracking ethane to ethylene at about 1800° F., in the presence of steam and added sulfur, this tube section has lower coking tendencies than the uncoated HP-50 steel sections.

EXAMPLE 4

A Chromium Plated and Heat Treated HP-50 Steel

A section of a furnace tube made of HP-50 Steel was cleaned and then electroplated to produce a hard chromium coating. The thickness of the coating was between 75 and 100 microns. This section was welded into the furnace tube in an ethylene cracking unit, and then heated to 1500° F. in oxygen-free argon for 4 hrs. (Hydrogen heat treatment can also be used).

After cracking ethane to ethylene at about 1800° F., in the presence of steam and added sulfur, this tube section has lower coking tendencies than the uncoated HP-50 steel sections and the chromium layer does not readily peel off.

EXAMPLE 5

Filling Cracks by Carbiding A Chromium Plated HP-50 Steel

A section of a furnace tube made of HP-50 Steel was cleaned and then electroplated to produce a hard chromium coating. The thickness of the coating was between 75 and 100 microns. This section is heated in hydrogen to 1600° F. and then treated with oxygen-free, water-free ethane for 4 hrs. This section is welded into the furnace tube in an ethylene cracking unit.

After cracking ethane to ethylene at about 1800° F., in the presence of steam and added sulfur, this tube section has lower coking tendencies than the uncoated HP-50 steel sections and the chromium layer does not readily peel off.

EXAMPLE 6

Filling Cracks by Nitriding A Chromium Plated HP-50 Steel

A section of a furnace tube made of HP-50 Steel was cleaned and then electroplated to produce a hard chromium coating. The thickness of the coating was between 75 and 100 microns. This section is heated to 1600° F. and is then treated with an oxygen-free, water-free nitrogen atmosphere for 4 hrs. This section is welded into the furnace tube in an ethylene cracking unit.

After cracking ethane to ethylene at about 1800° F., in the presence of steam and added sulfur, this tube section has lower coking tendencies than the uncoated HP-50 steel sections and the chromium layer does not readily peel off.

EXAMPLE 7

Coking of Chromium and Aluminum Oxides

A tube furnace experiment was run with various powdered metal oxides, including $Cr_2O_3$ and $Al_2O_3$ with 7% propane in hydrogen bubbled through one liter of water at room temperature so as to incorporate about 2% $H_2O$ (about 0.3 steam to hydrocarbon ratio) at 1600° F. for 4 hours. Petrographic microscopy analysis revealed that coke deposited on both the chromium oxide particles and the aluminum oxide particles. This example showed that undesirable coke deposits form on chromium and aluminum oxides at ethylene plant process conditions. These deposits, for example, will hinder hat transfer.

EXAMPLE 8

Chromium on HP-50 Steel

A tube furnace experiment was run with chromium metal plate on HP-50 steel and 7% propane in hydrogen at 1600° F. for 4 hours. Virtually no coke formed on the chromium metal plate. In the absence of steam, the chromium was coke free.

EXAMPLE 9

Steam Oxidation of Chromium and Aluminum

A tube furnace experiment was run with chromium metal plate on HP-50 steel and an aluminide coating on another HP-50 steel sample and a mixture of 1 to 1 hexane in hydrogen at 1800° F. for 24 hours. Coke deposits formed on the treated samples. Petrographic microscopy analysis revealed that coke had formed an oxidic alteration that had formed on the chromium plate and aluminide coating, respectively.

Apparently, in the presence of abundant steam, protective coatings of chromium or aluminide become oxidized and generate coke deposits under cracker conditions.

EXAMPLE 10

Loss of Chromium Layer

A tube furnace experiment was run with several samples of chromium metal-plated HP-50 coupons at 1800° F. and a mixture of 1/1 $H_2O$/hexane for 24 hours followed by coke burns at 1500° F. in 1/1 steam/air for 5 hours. Samples were removed after various numbers of cycles. Petrographic microscopy analysis revealed that over time the chromium coating oxidizes, is consumed, and disappears. Oxidation also occurs deeply within cracks in the chromium plate and along the interface with the underlying steel, which promotes premature peeling of the protective plate.

This experiment shows that abundant steam consumes the protective chromium plate over time and also induces catastrophic flaking.

EXAMPLE 11

Loss of Aluminide Layer

A tube furnace experiment was run with several samples of aluminided HP-50 steel under identical conditions as described in example 10. Over time the aluminide coating was oxidized away. This experiment shows that abundant steam consumes a protective aluminide coating over time.

EXAMPLE 12

Durability of Tin Coating

A tube furnace experiment was run with tin plate on type 304 stainless steel screen under 1% methyl benzene in 7% propane in hydrogen at 1150° F. for 14 weeks (the propane in hydrogen gas was bubbled through pure methyl benzene at room temperature to pick up approximately 1% by volume methyl benzene). Petrographic microscopy analysis of the stainless steel screen sample revealed that a nickel iron stannide protective coating about 10 µm thick had formed on the steel. The coating was utterly continuous. This example shows that tin coatings are durable in the absence of steam.

EXAMPLE 13

Styrene Selectivities

Two 52"×1" ID pilot plant reactors were prepared from 304 SS; the predominant metallurgy in a commercial styrene plant. Each reactor was filled with ⅛" 304 SS Helice packing from Ace Glass Co. The two reactor assemblies were identical except that one reactor ID and packing was coated with tin.

The tin coated materials were prepared using a tin paint. The paint consisted of a mixture of 2 parts powdered tin oxide, 2 parts finely powdered tin (1–5 microns), 1 part stannous neodecanoate in neodecanoic acid (20% Tin Tem-Cem sold by Mooney Chemical Company) mixed with isopropanol, as described in WO 92/15653. The reactor and packing were first cleaned with acetone to remove any residual oils, then coated with paint and drained. They were then heated in $H_2$ at 1100° F. for 48 hours. After cooling the materials were again cleaned with acetone.

The reactors were positioned inside a 3 zone Lindberg furnace at 1300° F. The ethylbenzene was preheated to 600° F. and mixed with steam that had been preheated to 800° F. The mixture was heated further by a transfer line heater before being fed to the reactor.

The reactors were run for about one week at the following conditions: ethylbenzene flow rate, gm/hr=30; water flow rate, gm/hr=45; steam/ethylbenzene wt/wt=1.5; exit pressure, mm Hg=760; and temperature=1300° F. These conditions were chosen to favor thermal reactions and to produce significant gas reaction products. The reaction products were cooled to about 35° F.

Table I shows the product selectivity for both the un-coated and coated reactors on a constant ethylbenzene feed basis. The data show the tin protected reactor reduced the conversion of ethylbenzene by about 4–5 percent. This lower ethylbenzene conversion is believed to result from a lower rate of metal catalyzed reactions. A comparison of the pilot plant product compositions show a 23 percent reduction in (undesirable) total gas selectivity. Individual selectivities to carbon monoxide, carbon dioxide, methane, and ethane were reduced by 40–60 percent. Thus, compared to a typical stainless steel plant, a stannided stainless steel plant produced less light gas—$CH_4$, CO, etc.

Table I also summarizes the results on a constant styrene product basis. These data show that for an equivalent styrene production, toluene and total heavies are reduced by 8–9 percent. Ethylbenzene consumption and benzene production were reduced by 5–6 percent. Total gas reactions were reduced by 28 percent.

After this procedure was completed, the reactor was cut open and the resulting layer was examined visually. Cross-sections of the steel were mounted in epoxy and polished. They were then examined using petrographic and scanning electron microscopy.

Petrographic microscopy analysis of steel from the two plants showed that the stainless steel plant was (unfortunately) deeply oxidized by steam in the reducing environment (1.5 steam/ethylbenzene, 1300° F.) to a depth of 50 µm. Some coke formed on the oxide coating. Most of the coke appeared to be thermal or acid-site derived, some was metal catalyzed. The oxide had a typical composition of: outer—99% Fe oxide; inner 35% Cr, 47% Fe, and 18% Ni oxides.

TABLE 1

Un-coated vs Tin-Coated Reactor

| Selectivities | UnCoated Reactor | Coated Reactor | DELTA | DELTA % |
|---|---|---|---|---|
| Product Selectivity, wt % | | | | |
| EB Conversion | 80.0 | 76.6 | −3.4 | −4.3 |
| Styrene | 42.4 | 44.7 | 2.4 | 5.6 |
| Benzene | 22.3 | 22.2 | −0.1 | −0.6 |
| Toluene | 9.8 | 9.5 | −0.3 | −3.3 |
| Heavy | 21.1 | 20.3 | −0.8 | −3.9 |
| Gas | 4.7 | 3.6 | −1.1 | −23.1 |
| Gas Selectivity, wt % | | | | |
| Methane | .9 | 0.69 | −0.51 | −42.5 |
| Carbon Monoxide | 0.04 | 0.01 | −0.03 | −66.9 |
| Carbon Dioxide | 0.26 | 0.06 | −0.20 | −76.1 |
| Ethylene | 1.73 | 1.81 | 0.07 | 4.4 |
| Ethane | 0.53 | 0.23 | −0.30 | −56.4 |
| Per 100 lbs Styrene, lb | | | | |
| EB used | (236.1) | (223.6) | (12.5) | −5.3 |
| Toluene made | 23.1 | 21.1 | 1.9 | −8.4 |
| Benzene made | 52.7 | 49.5 | 3.1 | −5.9 |
| Heavies made | 49.9 | 45.4 | 4.5 | −9.0 |
| HC to vent gas | (10.5) | (7.6) | (3.0) | −28.3 |

Petrographic microscopy analysis of the stannided packing from the tin-treated system revealed that the steel was uniformly oxidized to a depth of about 30 µm, although a continuous, protective coating of stannide remained. The inner oxide here was: 18% Cr, 75% F, 0.1% Ni, and 8% Sn oxides typically. Under the oxide was a layer of pure nickel-iron stannide, which was continuous and unbreached. We believe that the stannide layer would protect the underlying steel from further oxidative attack by steam and that with reduced steam levels little, if any, oxide would have formed in the first place. This example shows that tin coatings improve the commercial practice and are durable, with the implication that tin would be better with less steam.

While the invention has been described above in terms of preferred embodiments, it is to be understood that variations and modifications may be used as will be appreciated by those skilled in the art. Indeed, there are many variations and modifications to the above embodiments which will be readily evident to those skilled in the art, and which are to be considered within the scope of the invention as defined by the following claims.

What is claimed is:

1. A improved steam reforming process, comprising
    a) operating a steam reforming process in a steam reforming reactor system at a first steam to carbon ratio;
    b) providing a protective layer to at least a portion of said steam reforming reactor system, wherein said layer was prepared by applying a plating, cladding, paint or other coating to at least a portion of a steam reforming reactor system, said protective layer being effective to reduce the amount of undesirable by-products in said process; and
    c) operating the steam reforming process at a second steam to hydrocarbon ratio that is at least 5% lower than said first steam to carbon ratio.

2. The improved steam reforming process of claim 1 wherein the plating, cladding, paint or other coating is a metal plating, cladding, paint or other coating.

3. An improved commercial scale steam reforming process, comprising providing a metallic protective layer to a steel portion of a steam reforming reactor system, wherein said layer was prepared by applying a metal plating, cladding, paint or other coating to at least a portion of a steam reforming reactor system, said coating being effective to reduce the amount of undesirable by-products in said process; and using said protected reactor system for steam reforming at low steam to carbon ratios.

4. The improved steam reforming process of claim 1 or 2 wherein the second steam to carbon ratio is about 2.5.

5. The improved steam reforming process of claim 1 or 2 wherein the second steam to carbon ratio is about 2.

6. The improved steam reforming process of claim 1 or 2 wherein the second steam to carbon ratio is about 1.

7. The improved steam reforming process of claim 3 wherein the steam to carbon ratio is about 2.5.

8. The improved steam reforming process of claim 3 wherein the steam to carbon ratio is about 2.

9. The improved steam reforming process of claim 3 wherein the steam to carbon ratio is about 1.

10. The improved steam reforming process of claim 2 or 3 wherein the coating contains a metal selected from the group consisting of tin, antimony, germanium, arsenic, aluminum, gallium, indium, copper, chromium, molybdenum, tungsten, silicon, titanium, niobium, zirconium, tantalum, hafnium, bismuth, indium and lead, and mixtures, intermetallic compounds and alloys thereof.

11. The improved steam reforming process of claim 2 or 3 wherein the coating contains a metal selected from the group consisting of tin, antimony, chromium and aluminum, and mixtures, intermetallic compounds and alloys thereof.

12. The improved steam reforming process of claim 2 or 3 wherein the coating contains a metal selected from the group consisting selected from chromium and aluminum, and mixtures, intermetallic compounds and alloys thereof.

13. The improved steam reforming process of claim 2 or 3 wherein the metal coating contains tin.

14. The improved steam reforming process of claim 2 or 3 wherein the metal coating contains chromium.

15. The improved steam reforming process of claim 2 or 3 wherein the metal-containing plating, cladding, paint or other coating is applied to at least one surface of a furnace tube.

16. The improved steam reforming process of claim 1 or 2 or 3 wherein the protective layer has a thickness effective to isolate the steel portion from hydrocarbons during operation and is anchored to the steel portion through an intermediate carbide-rich bonding layer.

17. The improved steam reforming process of claim 1 or 2 or 3 wherein the steam reforming process utilizes natural gas.

18. The improved steam reforming process of claim 2 or 3 wherein the coating contains a metal selected from the group of elements consisting of bismuth, indium and lead, and wherein the coating is applied to a steel portion that contains greater than 50% nickel.

* * * * *